(12) United States Patent
Allen et al.

(10) Patent No.: US 10,669,521 B2
(45) Date of Patent: Jun. 2, 2020

(54) PRE-FABRICATED MULTI-MODAL BIOENERGY SYSTEMS AND METHODS

(71) Applicant: Impact Bioenergy Inc., Shoreline, WA (US)

(72) Inventors: Jan Allen, Shoreline, WA (US); Connor Folley, Shoreline, WA (US); Thomas Kraemer, Duvall, WA (US)

(73) Assignee: IMPACT BIOENERGY, INC., Shoreline, WA (US)

( * ) Notice: Subject to any disclaimer, the term of this patent is extended or adjusted under 35 U.S.C. 154(b) by 0 days.

(21) Appl. No.: 15/706,525

(22) Filed: Sep. 15, 2017

(65) Prior Publication Data
US 2018/0030399 A1    Feb. 1, 2018

Related U.S. Application Data

(63) Continuation of application No. 14/156,704, filed on Jan. 16, 2014.

(51) Int. Cl.
| | | |
|---|---|---|
| *C05F 17/00* | (2020.01) | |
| *C12M 1/00* | (2006.01) | |
| *C05F 17/50* | (2020.01) | |
| *C05F 17/979* | (2020.01) | |
| *C05F 17/986* | (2020.01) | |

(52) U.S. Cl.
CPC ............. *C12M 43/02* (2013.01); *C05F 17/50* (2020.01); *C05F 17/979* (2020.01); *C05F 17/986* (2020.01); *Y02E 50/343* (2013.01); *Y02P 20/145* (2015.11); *Y02W 30/43* (2015.05); *Y02W 30/47* (2015.05); *Y10T 29/49826* (2015.01)

(58) Field of Classification Search
CPC ................ C05F 17/0027; C05F 17/027; C05F 17/0276; C12M 43/02
See application file for complete search history.

(56) References Cited

U.S. PATENT DOCUMENTS

| | | | | |
|---|---|---|---|---|
| 4,683,814 A | * | 8/1987 | Plovanich | B30B 9/20 100/121 |
| 4,752,316 A | * | 6/1988 | Plovanich | B30B 9/20 71/11 |
| 5,375,944 A | * | 12/1994 | Kotani | B09B 1/00 405/129.2 |
| 5,564,862 A | * | 10/1996 | Markels, Jr. | B09B 1/00 210/747.1 |
| 5,765,437 A | * | 6/1998 | Farber | A01B 1/065 408/1 R |
| 6,283,676 B1 | * | 9/2001 | Hater | B09B 1/00 210/747.1 |
| 6,364,572 B1 | * | 4/2002 | Hudgins | B09B 1/00 405/129.35 |
| 6,435,769 B2 | * | 8/2002 | Harrington | B09B 1/00 405/128.1 |
| 6,758,972 B2 | * | 7/2004 | Vriens | C02F 3/121 210/259 |

(Continued)

*Primary Examiner* — Benjamin F Fiorello

(57) ABSTRACT

Embodiments of this invention provide an apparatus that allows for the biodegrading of materials including food waste, food service paper products, wet waste, paper cardboard, landscape waste, and other organic solids using a prefabricated, multi-modal, portable, modular system that includes a series of bio-mimicry vessels in multiple mode deployment.

20 Claims, 18 Drawing Sheets

(56) References Cited

U.S. PATENT DOCUMENTS

| | | | |
|---|---|---|---|
| 8,662,791 B2* | 3/2014 | Allen | C05F 17/0027 405/129.57 |
| 2004/0047691 A1* | 3/2004 | Baumgartner | A01C 3/028 405/129.57 |
| 2004/0085013 A1* | 5/2004 | Han | H01L 51/5203 313/503 |
| 2004/0191755 A1* | 9/2004 | Kemper | B09B 1/00 435/3 |
| 2006/0010712 A1* | 1/2006 | Carin | C05F 3/00 34/443 |
| 2011/0005284 A1* | 1/2011 | Conner | C02F 3/1268 71/12 |
| 2011/0100924 A1* | 5/2011 | Duesel, Jr. | B01D 1/14 210/710 |

* cited by examiner

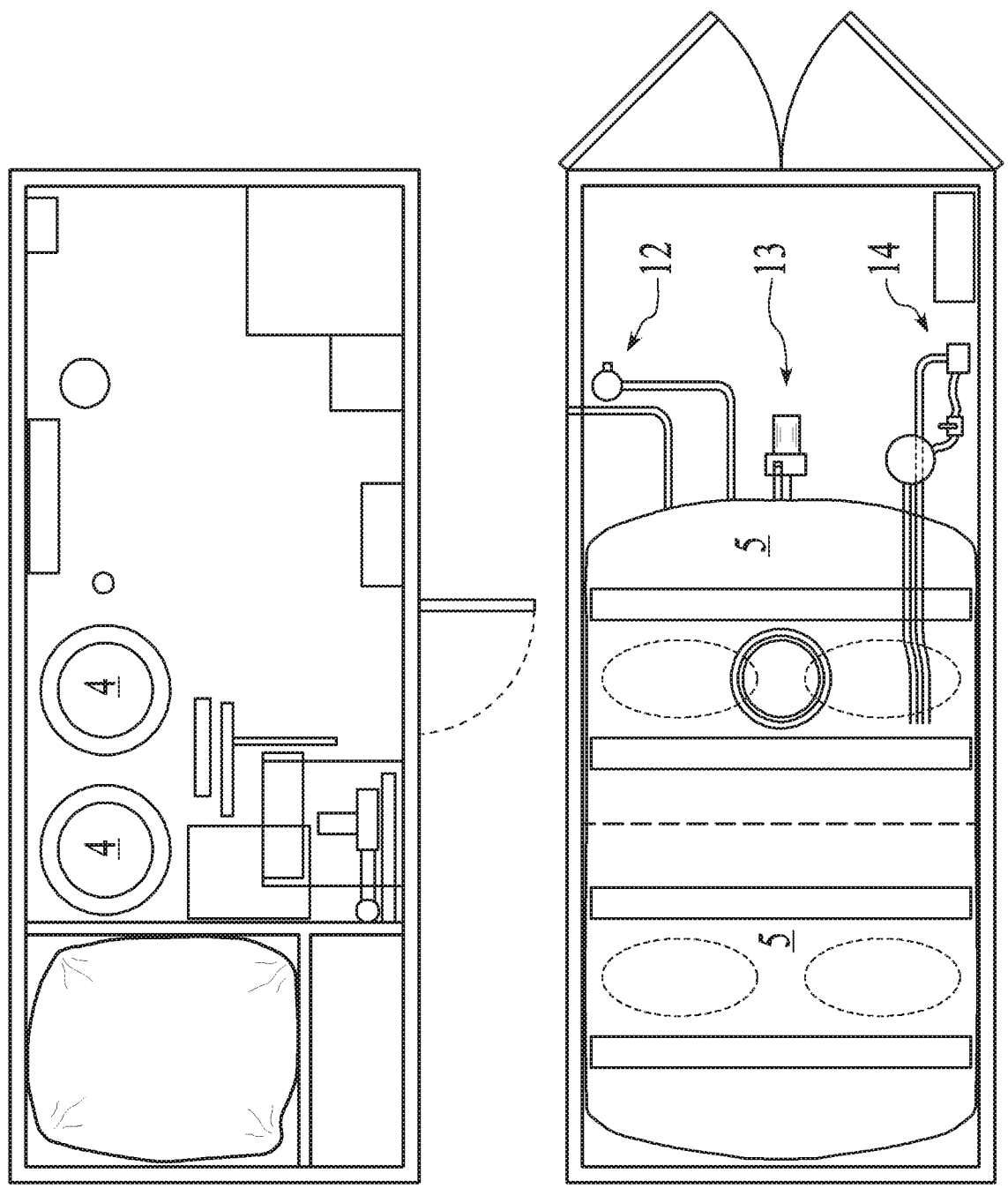

PRE-FABRICATED MULTI-MODAL BIOENERGY SYSTEMS AND METHODS

CROSS-REFERENCES TO RELATED APPLICATIONS

This application claims priority to U.S. Non-provisional application Ser. No. 14/156,704, filed Jan. 16, 2014, the disclosure of which is incorporated by reference herein in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND

Currently, anaerobic digestion, aerobic digestion, gasification, product-packaging separation, trans-esterification, drying, and prilling are used as independent processes. Each process requires feedstock as input and is designed to produce one or more marketable products as output. Additionally, each of these processes produces by-products (also called co-products) that may become commercially valuable product and a source of revenue, or an operating expense for disposal, or an environmental liability. Examples of these by-products are digestate (digestion yields), new soil product, new fuel product, bankable carbon to be sequestered, woody oversized particles (composting yield), ash (gasification yields), and glycerin (trans-esterification yields).

Generally, energy output is also considered a by-product. For example, heat production from composting, biogas from digestion, and syngas from gasification are by-products. Accessories fueled by biogas from digestion include hot water heaters, electricity generation, radiant space heaters, lighting, fireplaces or fire pits, barbeques, cooking equipment, and CNG vehicle fueling.

Organic waste processing facilities are typically designed at a scale of 100 to over 1,000 tons per day. They exist in four industrial sectors: wastewater treatment, manure treatment, industrial process plants, and urban organic recycling plants. These processing facilities control feedstock preparation, residence time, temperature, moisture, density, oxygen, pH, and particle size. They may also control odors, typically with a one-stage treatment system.

Commonly, design and deployment of facilities that employ anaerobic digestion, aerobic digestion, gasification, product-packaging separation, trans-esterification, drying, or prilling processes requires between 2 and 4 years from initial project kickoff to actual commissioning. They are also typically designed as large, centralized facilities based upon the presumption that larger facilities are more cost-efficient due to the larger economies of scale. This presumption has proven to be incorrect or erroneous in most urban organic recycling situations due to the high costs of odor control, the high costs of hauling and transportation of feedstocks (as inputs), and the high costs of hauling and transportation of by-products (as outputs) over increasingly longer distances.

In certain circumstances, or geographic areas, the construction of these types of facilities may also face an added set of problems as local conditions may make it extremely problematic sourcing the requisite materials for constructing the facilities, or constructing with poor weather conditions, or constructing with poor-quality geotechnical conditions. In such circumstances, prefabrication of portable systems reduces risk and ensures more reliable performance of facilities that employ anaerobic digestion, aerobic digestion, alternating digestion, gasification, product-packaging separation, trans-esterification, drying, or prilling processes.

There is a desire and need for renewable energy, energy independence, distributed energy generation, diversion of organic waste from disposal, and zero waste systems. ("Zero Waste Movement"). Coupling two or more of the above technologies (modes) together in a synergistic way to reduce by-product waste and increase usable energy/heat production will help achieve the goals of the Zero Waste Movement. For example, trans-esterification can benefit from a downstream anaerobic digester to convert surplus glycerin into valuable energy and fertilizer. The practice of coupling these technologies can be referred to as by-product synergy. The use of machinery that replicates natural systems that are similar to those used by plants or animals is referred to as bio-mimicry. For example, an anaerobic digester replicates a cow's gastrointestinal tract with regard to mastication, multiple stomachs, gas production, and fertilizer production.

There is also a need to install smaller scale digester bio-mimicry systems as stand-alone systems near locations where the waste products are generated to minimize or eliminate trucking waste. By delivering prefabricated smaller scale bio-mimicry systems to the point of use, reliable cost-efficient bio-mimicry systems may be employed by more users in more diverse locales. The combined effect of use of smaller scale multi-modal systems, the elimination of trucking costs, and prefabrication creates the benefit of lower risk, distributed utilities, and more local resiliency regarding jobs, energy, food, and other resources.

SUMMARY

An objective of this invention is to provide an apparatus that allows for the biodegrading of food waste, food service paper products, wet waste, paper cardboard, landscape waste, and other organic solids using a prefabricated, multi-modal, portable, modular system that includes a series of bio-mimicry vessels in multiple mode deployment ("Bioenergy System"). This prefabricated smaller scale modular Bioenergy System is capable of being transported by road, rail or sea, so as to be quickly deployed for use. Use of the Bioenergy System as envisioned will result in minimizing transportation costs and economic risks associated with the implementation of an organic waste processing facility.

DRAWINGS DESCRIPTION

Other features and advantages of the present invention will become apparent in the following detailed descriptions of certain preferred embodiments with reference to the accompanying drawings, of which:

FIG. 2 shows a plan view of a primary module of a two-digester-chamber bio-mimicry system using circular digester chambers in the primary module according to illustrative embodiments of the present invention;

FIG. 3 shows a plan view of a two-digester-chamber bio-mimicry apparatus with a large capacity, a capacity expansion module, with a level control apparatus, and with a mixing and digester heating apparatus, according to illustrative embodiments of the present invention;

Figure 4:
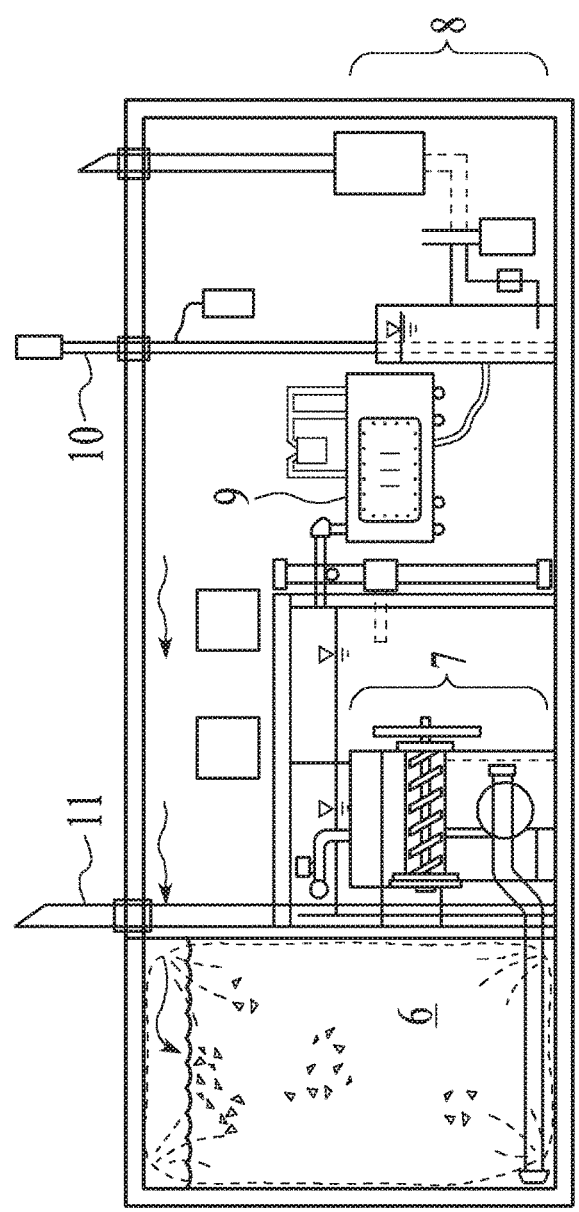
Figure 5:
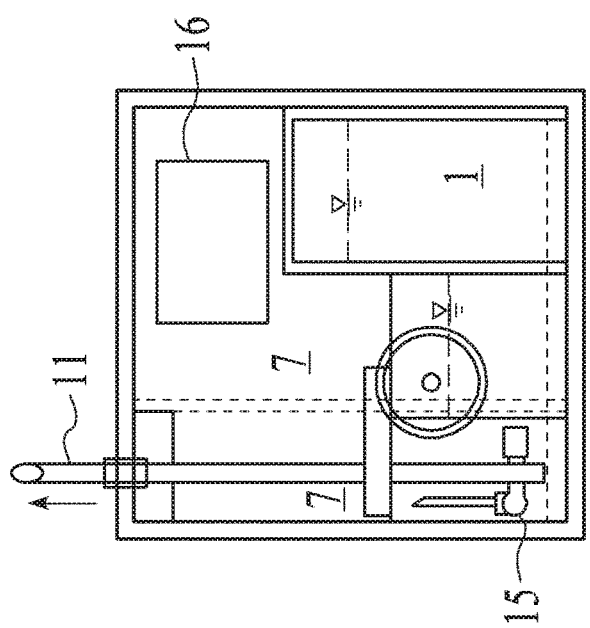
Figure 6:
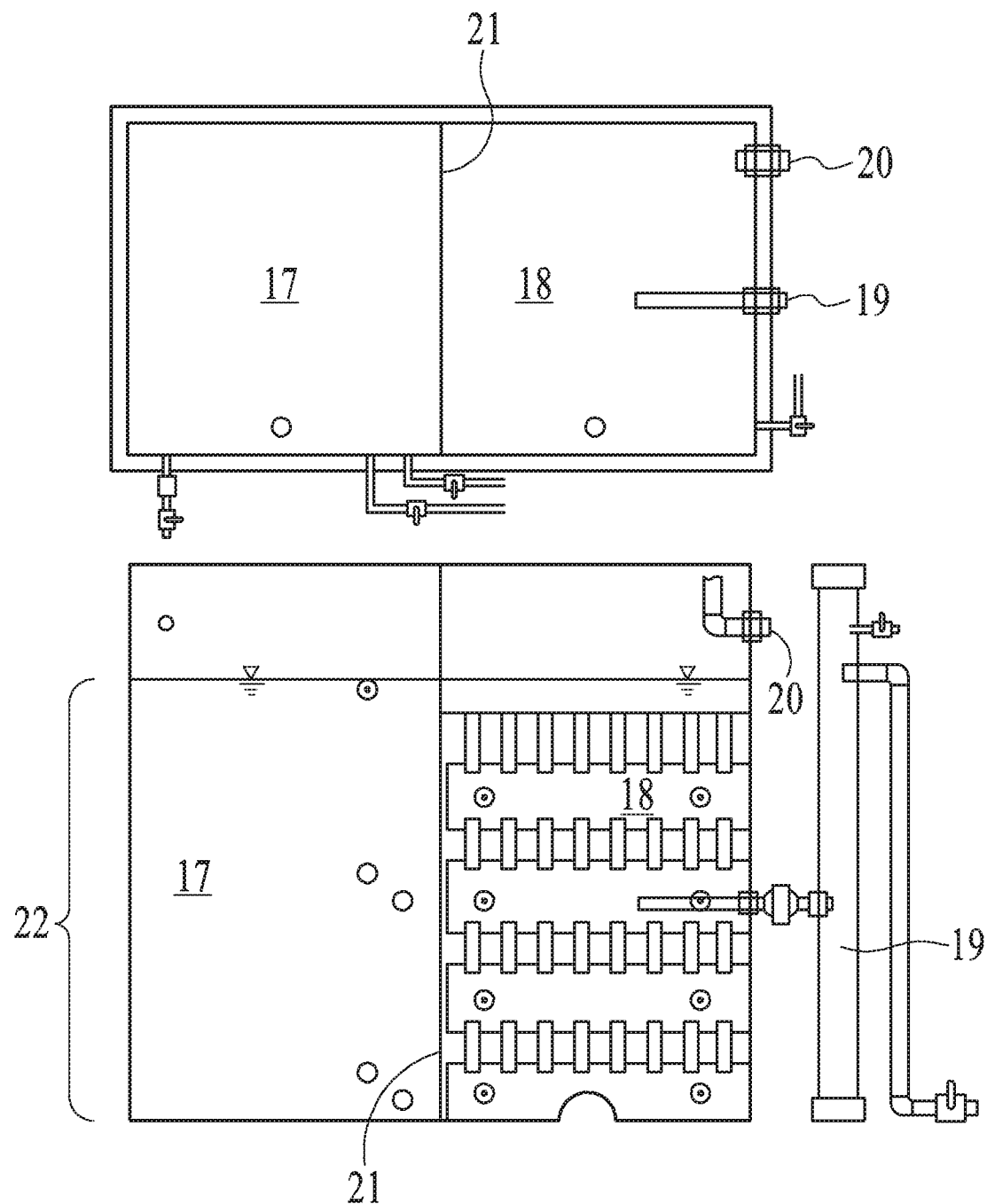
Figure 7:
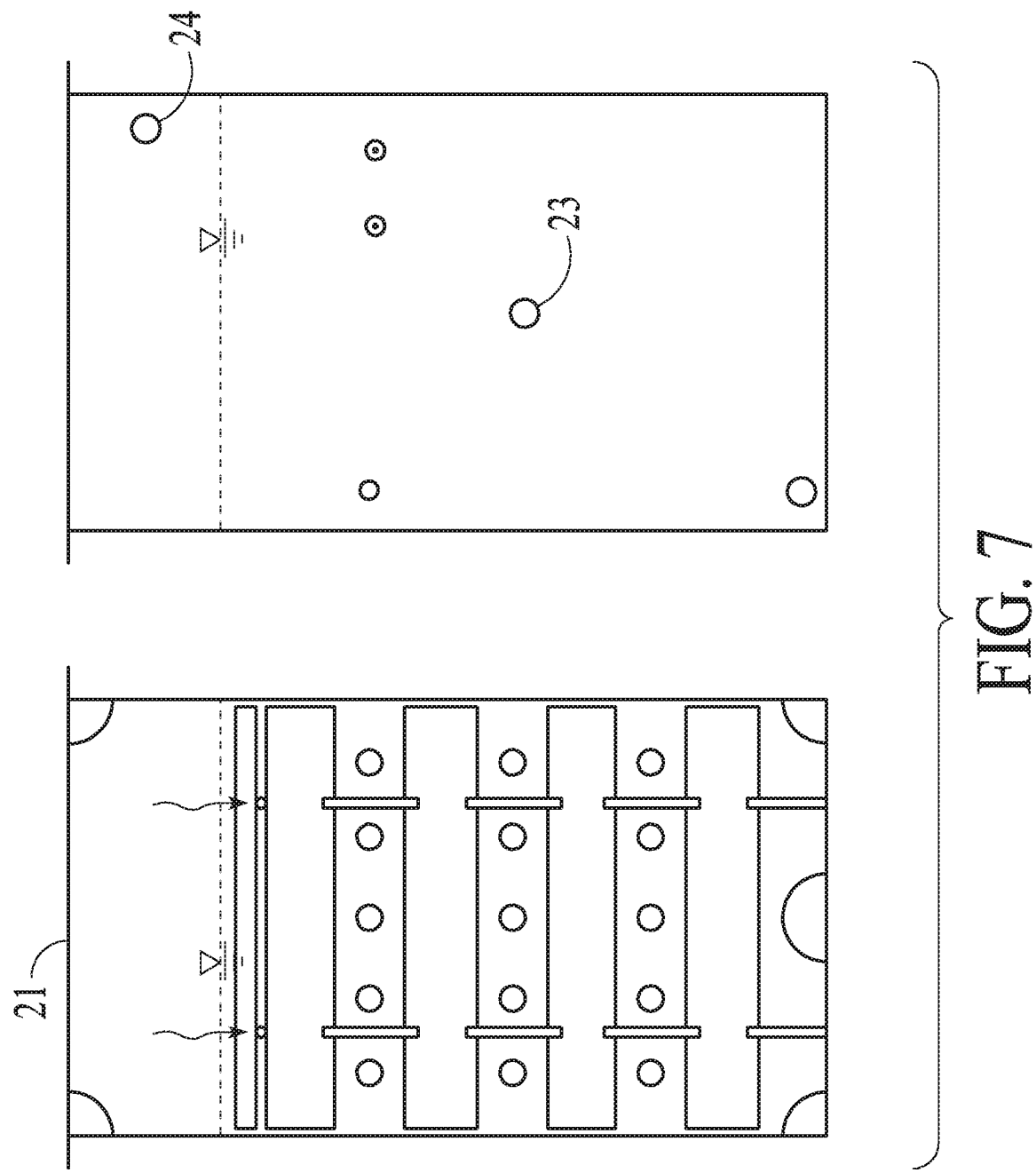
Figure 8:
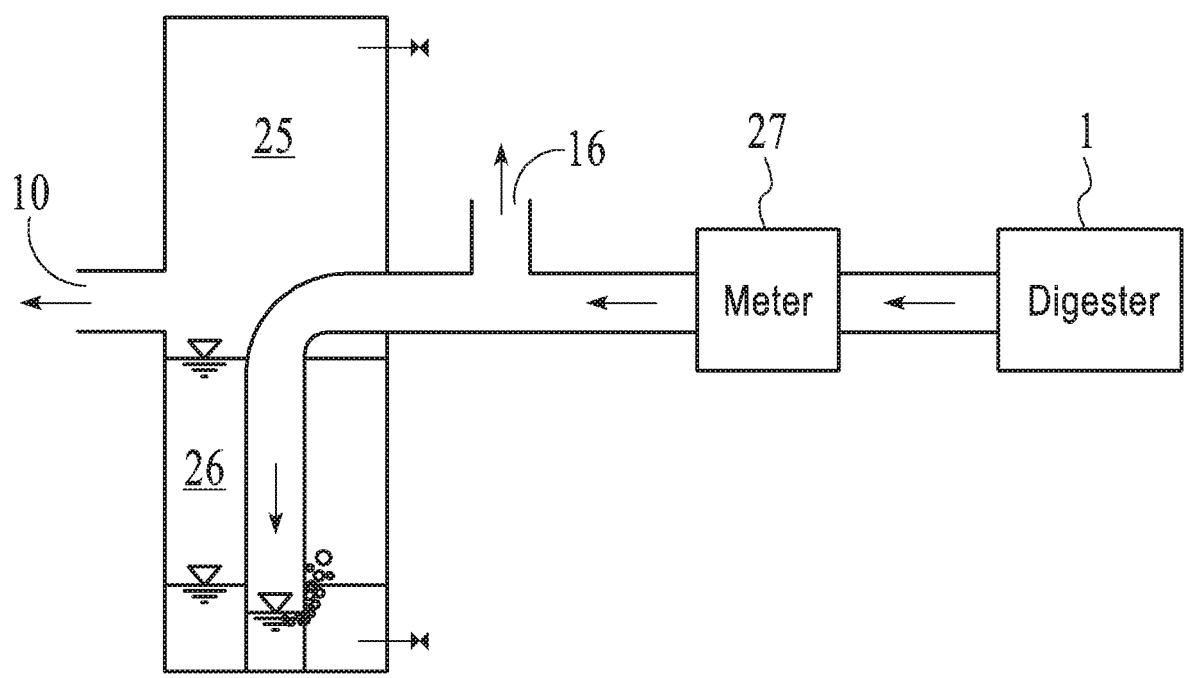
Figure 9:
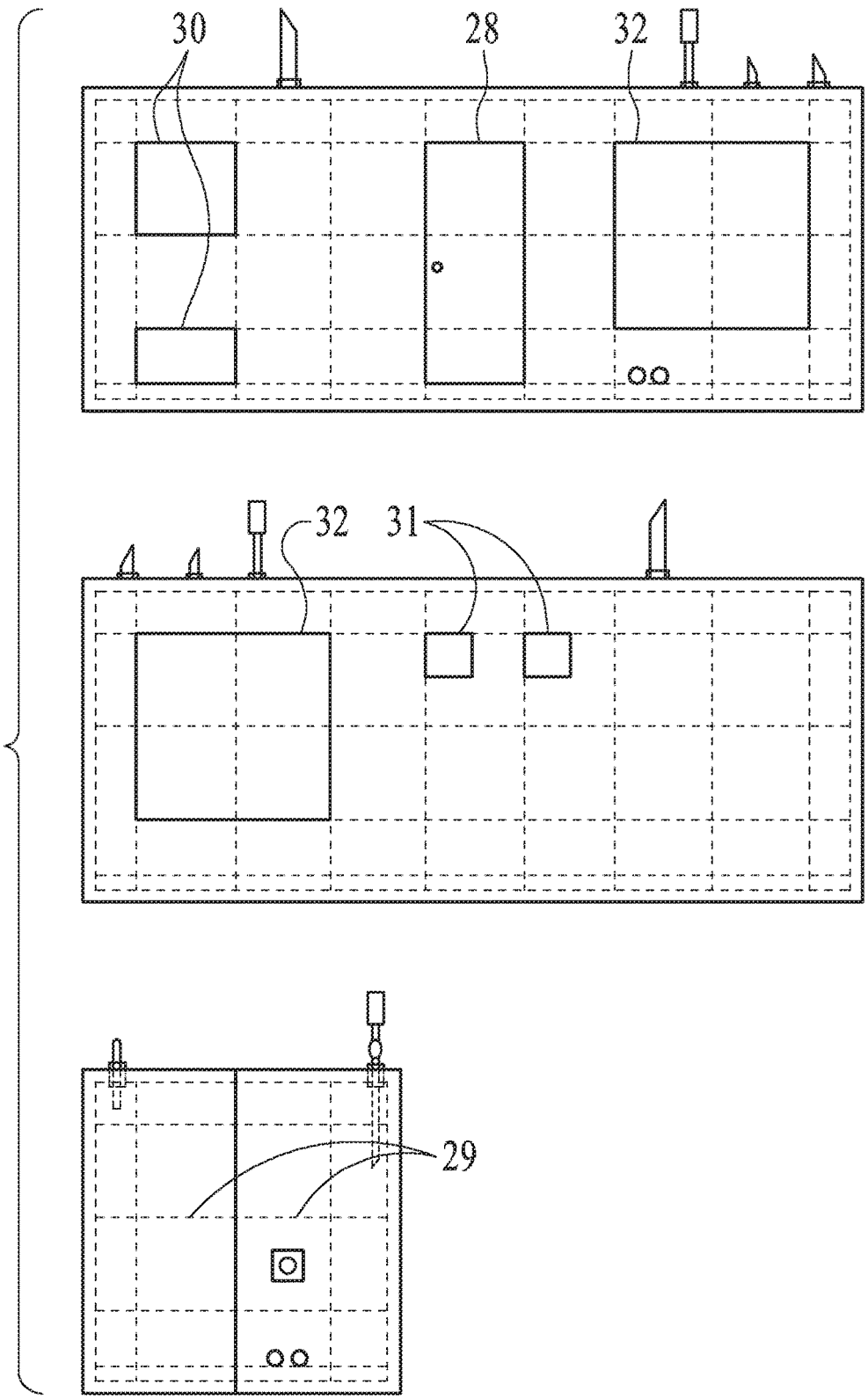
Figure 10:
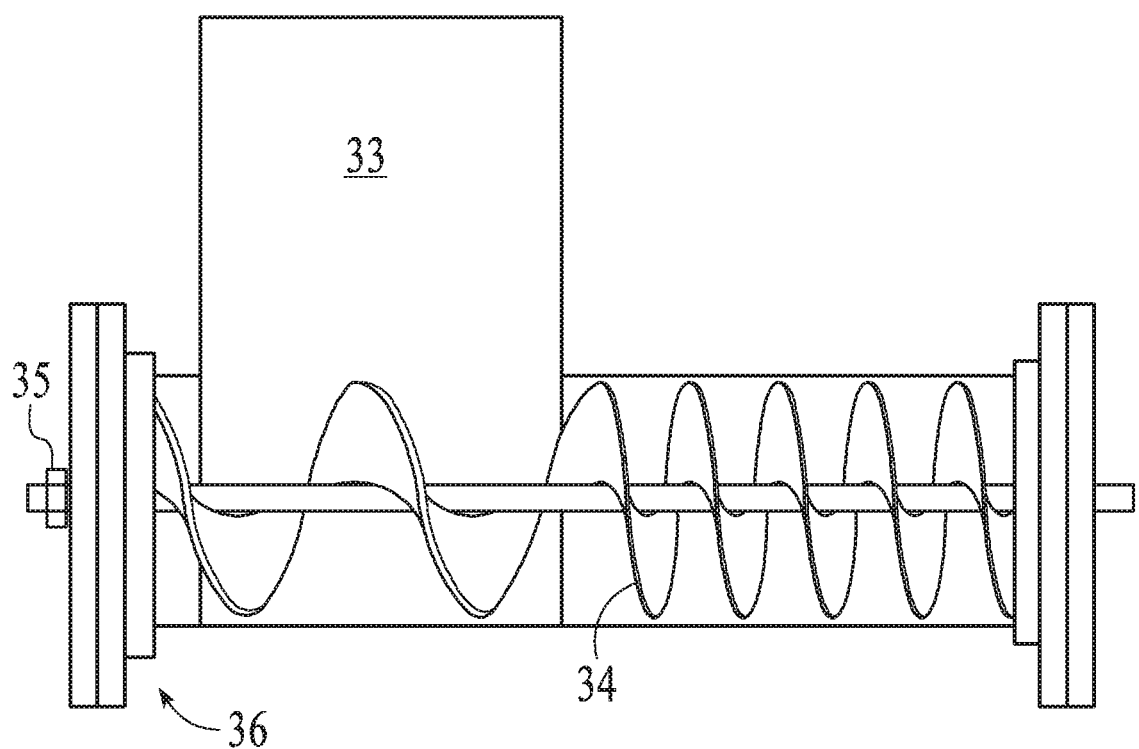
Figure 11:
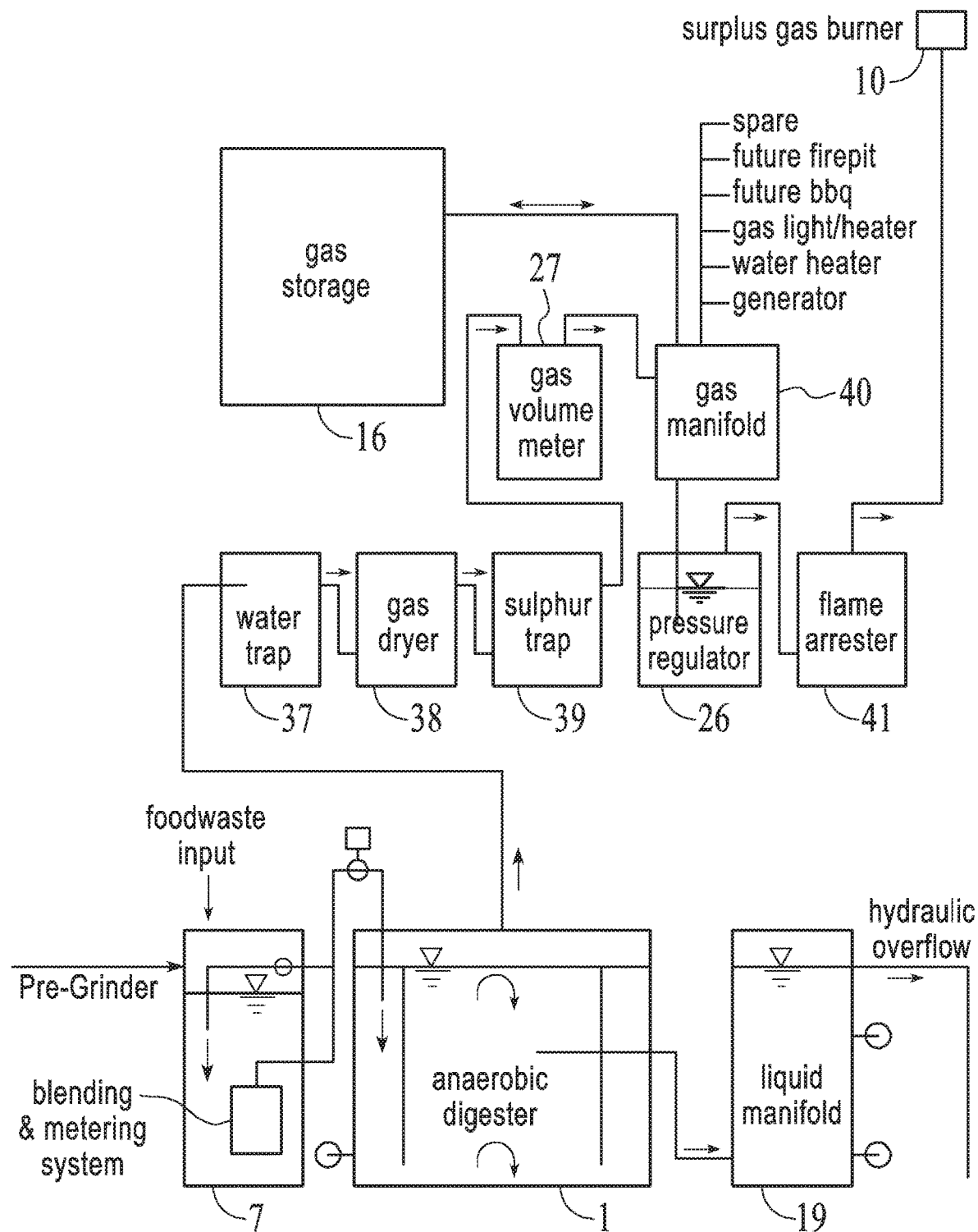
Figure 12A:
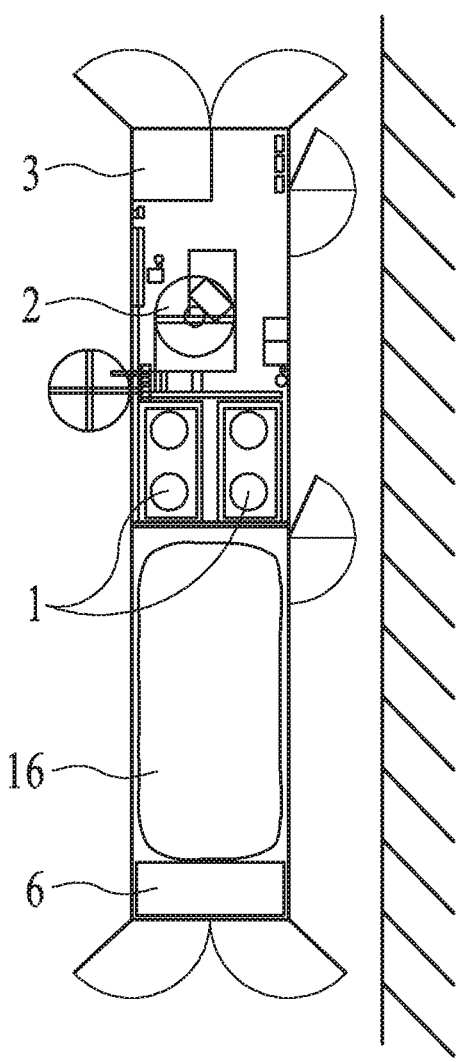
Figure 12B:
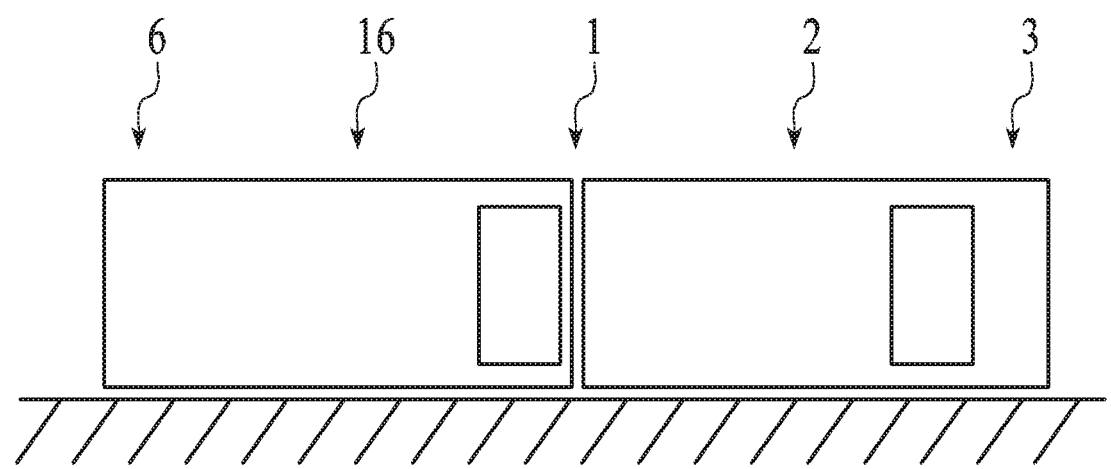
Figure 13A:
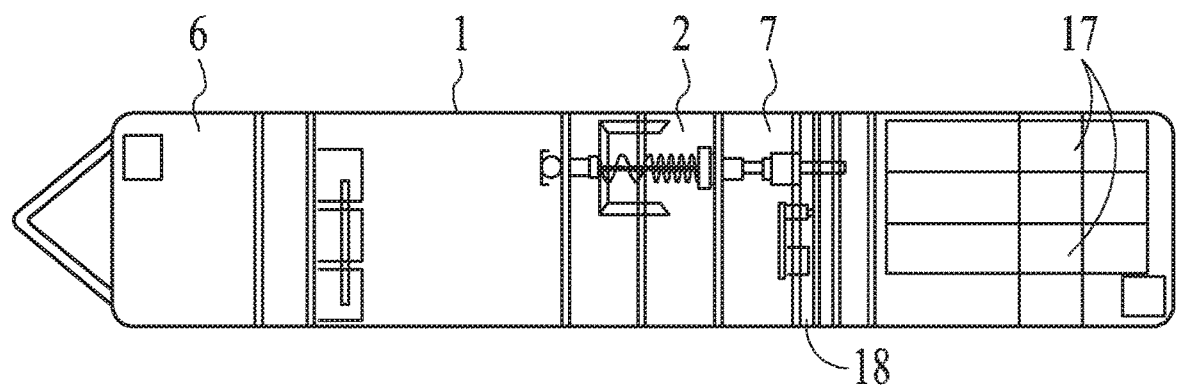
Figure 13B:
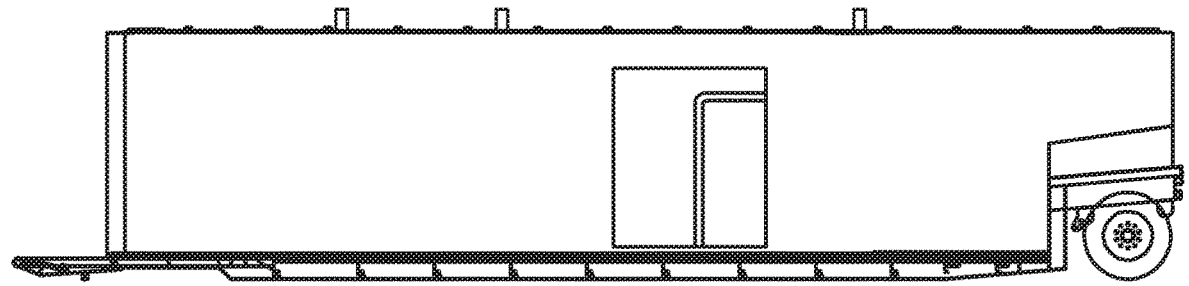
Figure 13C:
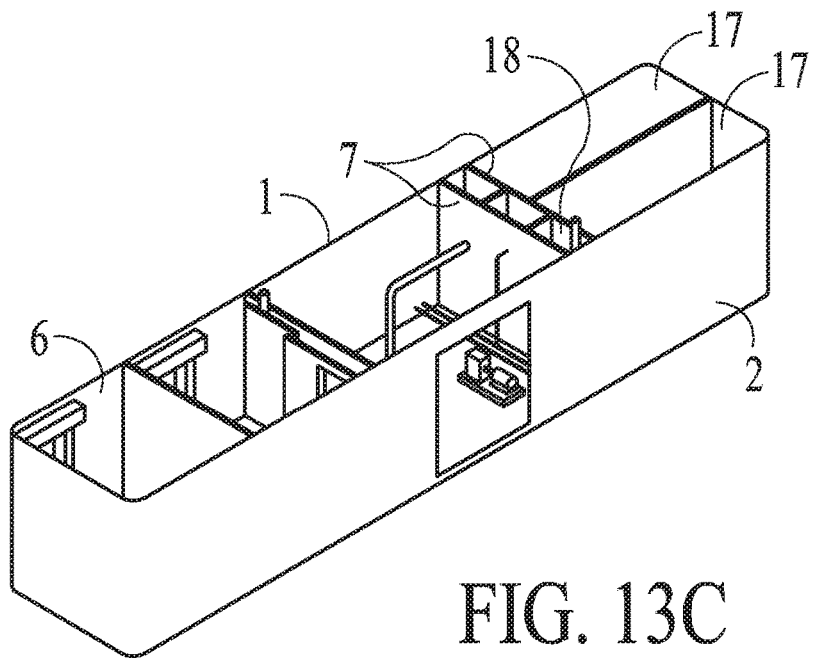
Figure 14:
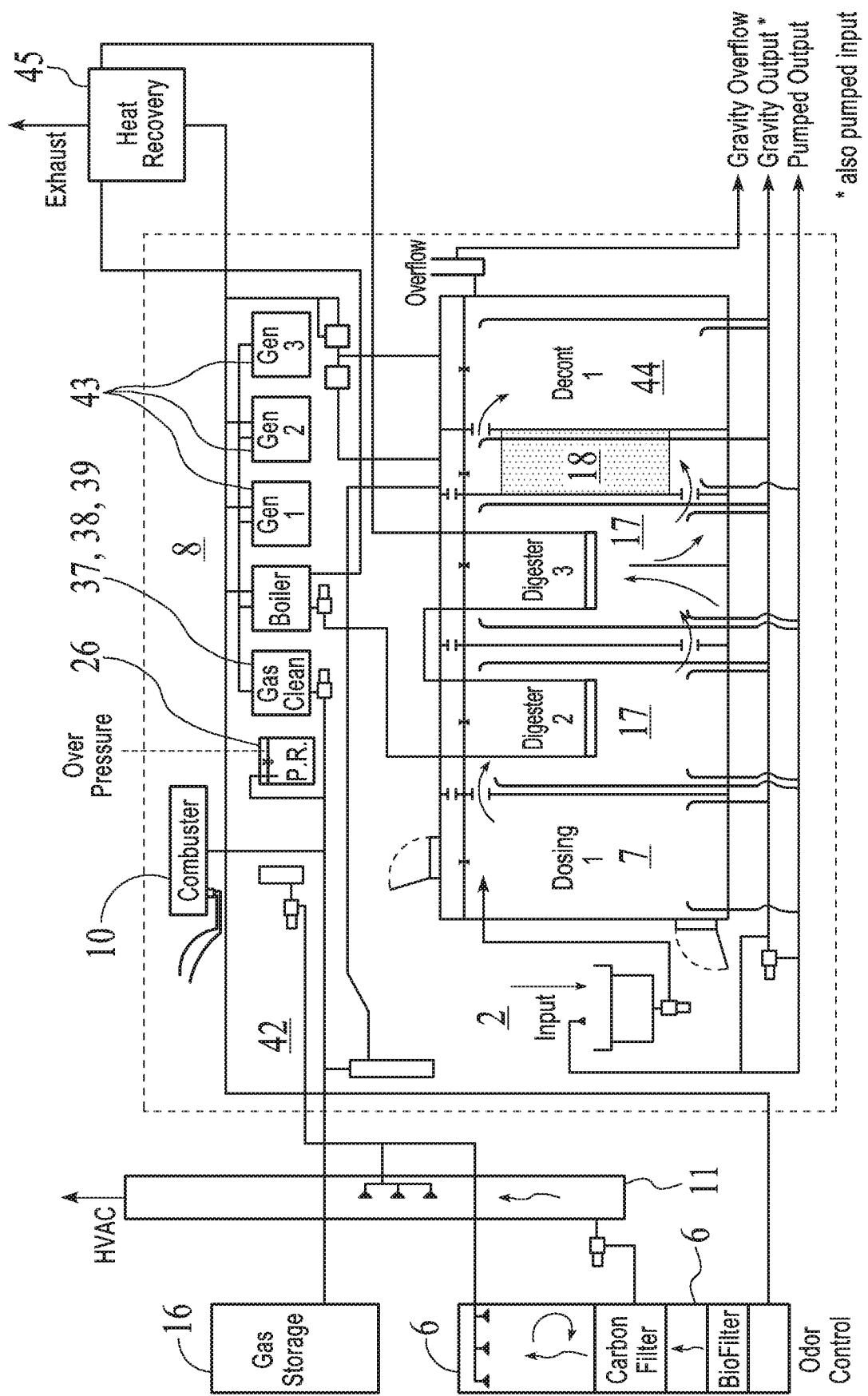
Figure 15:
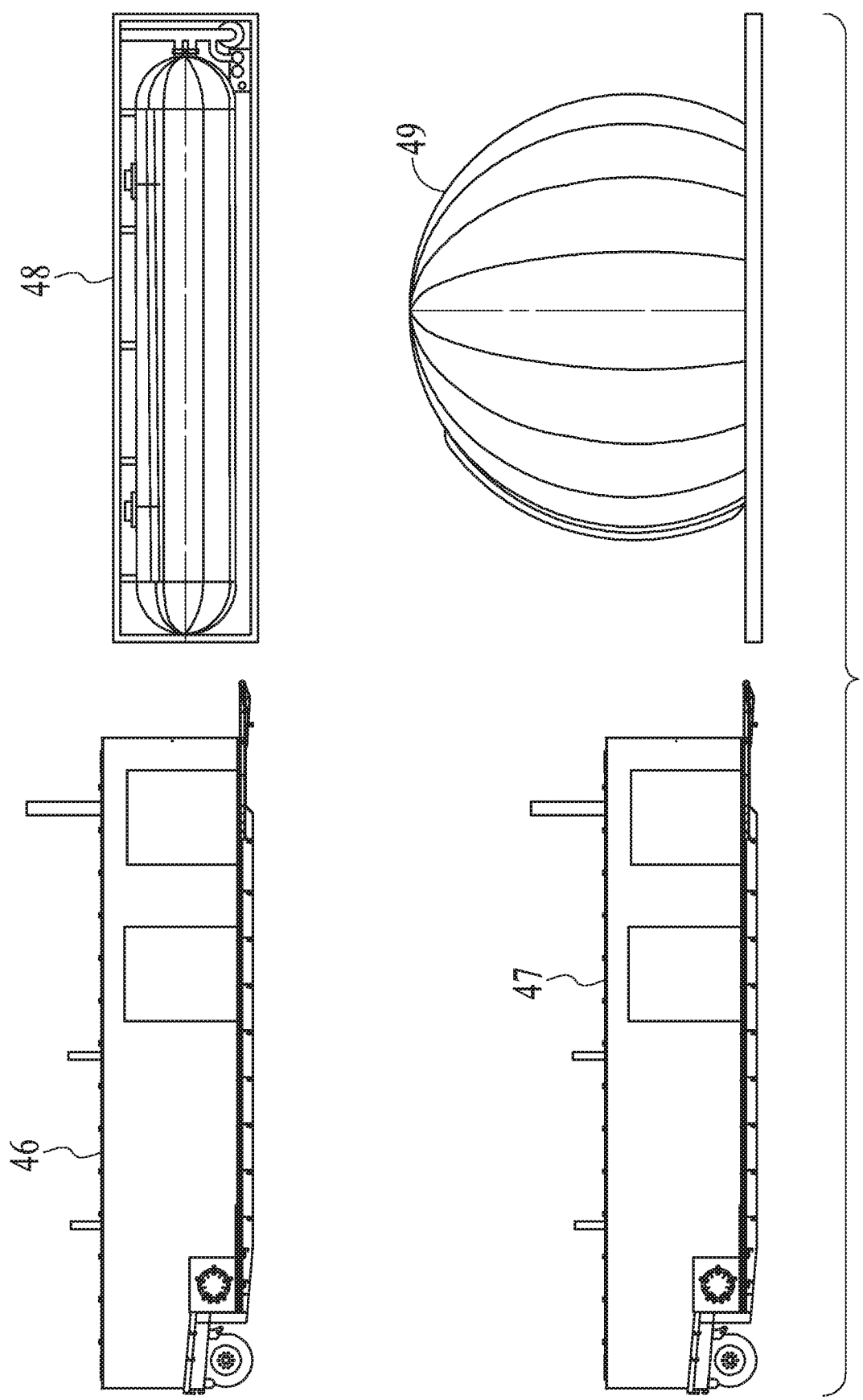
Figure 16:
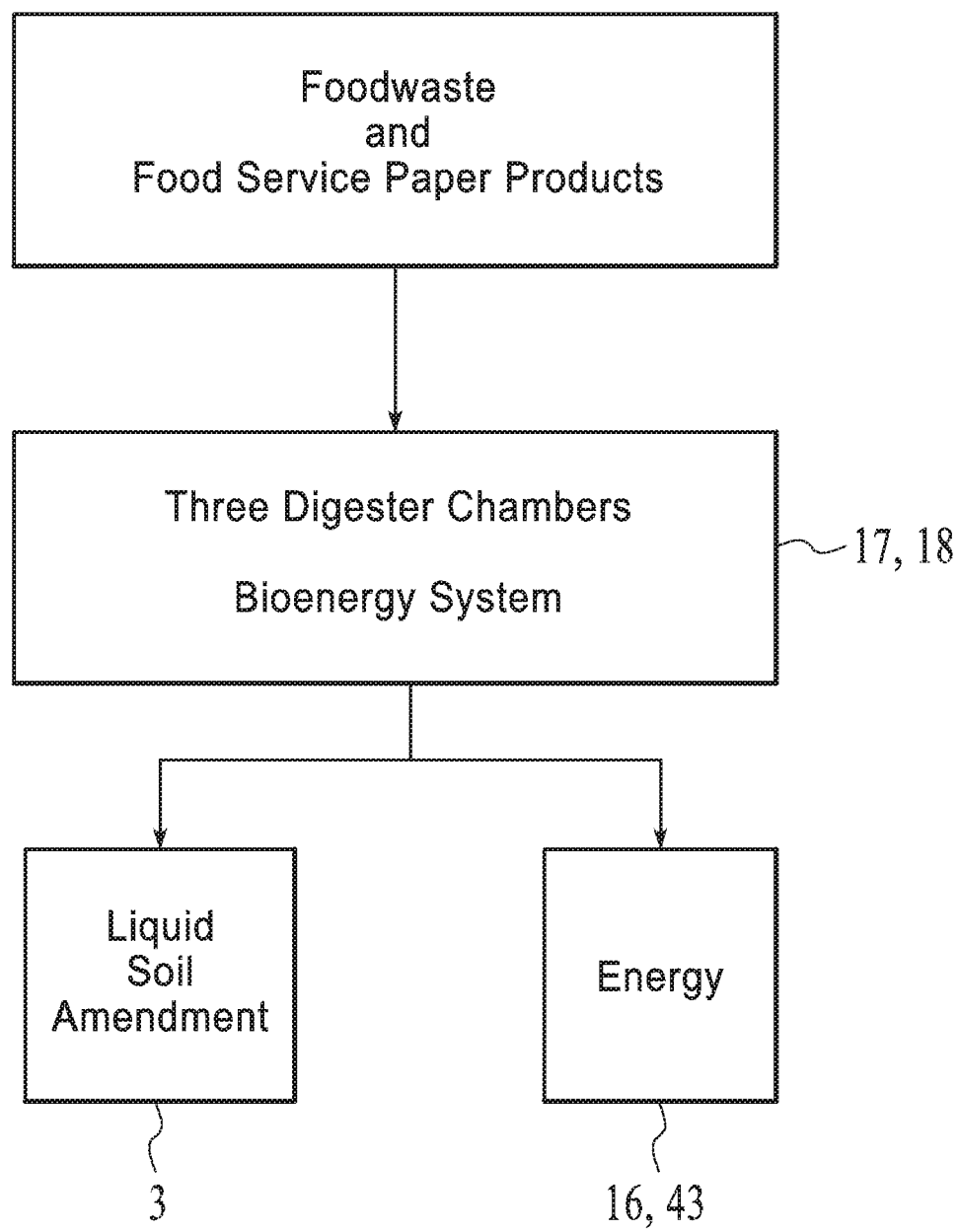
Figure 17:
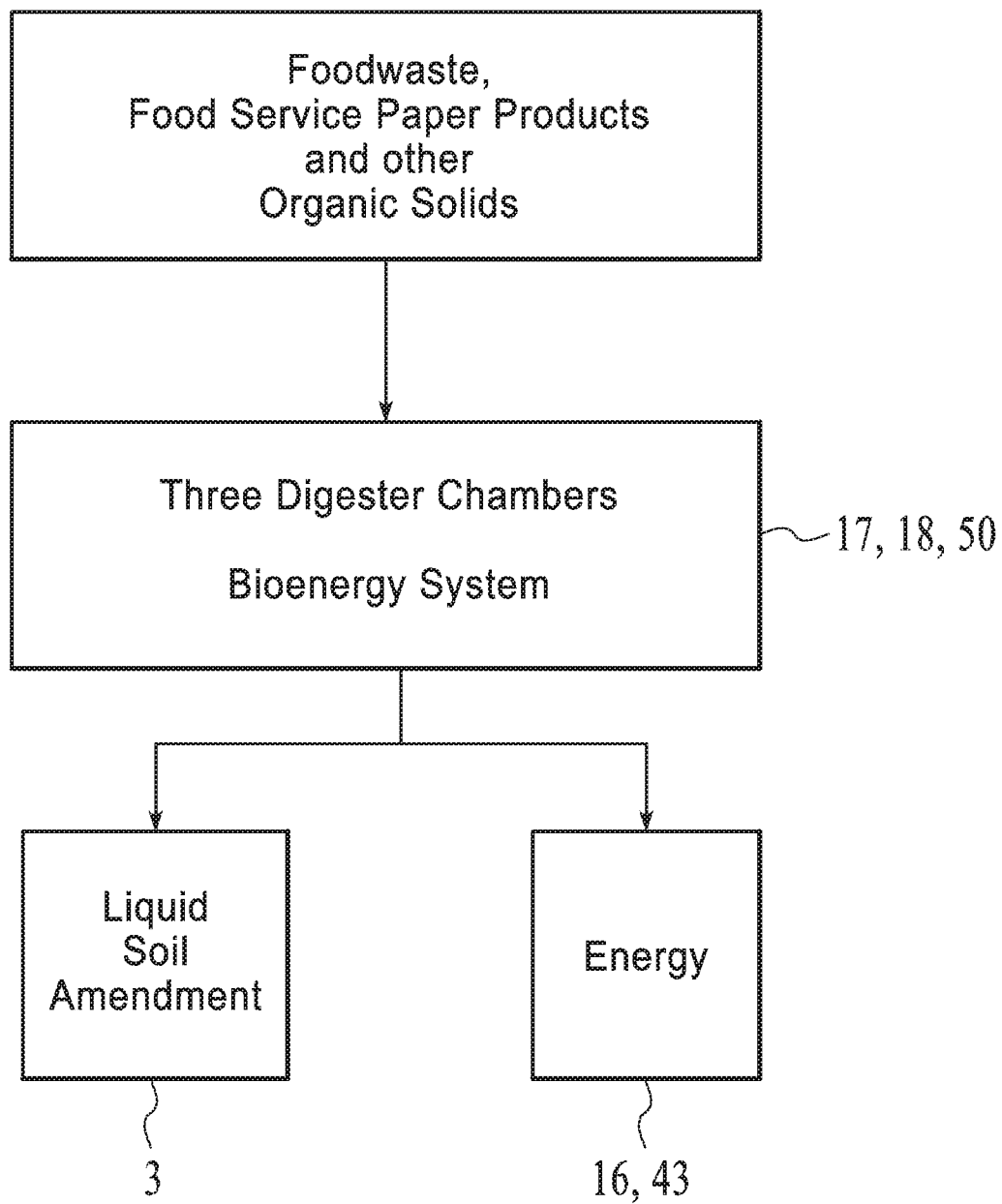
Figure 18:
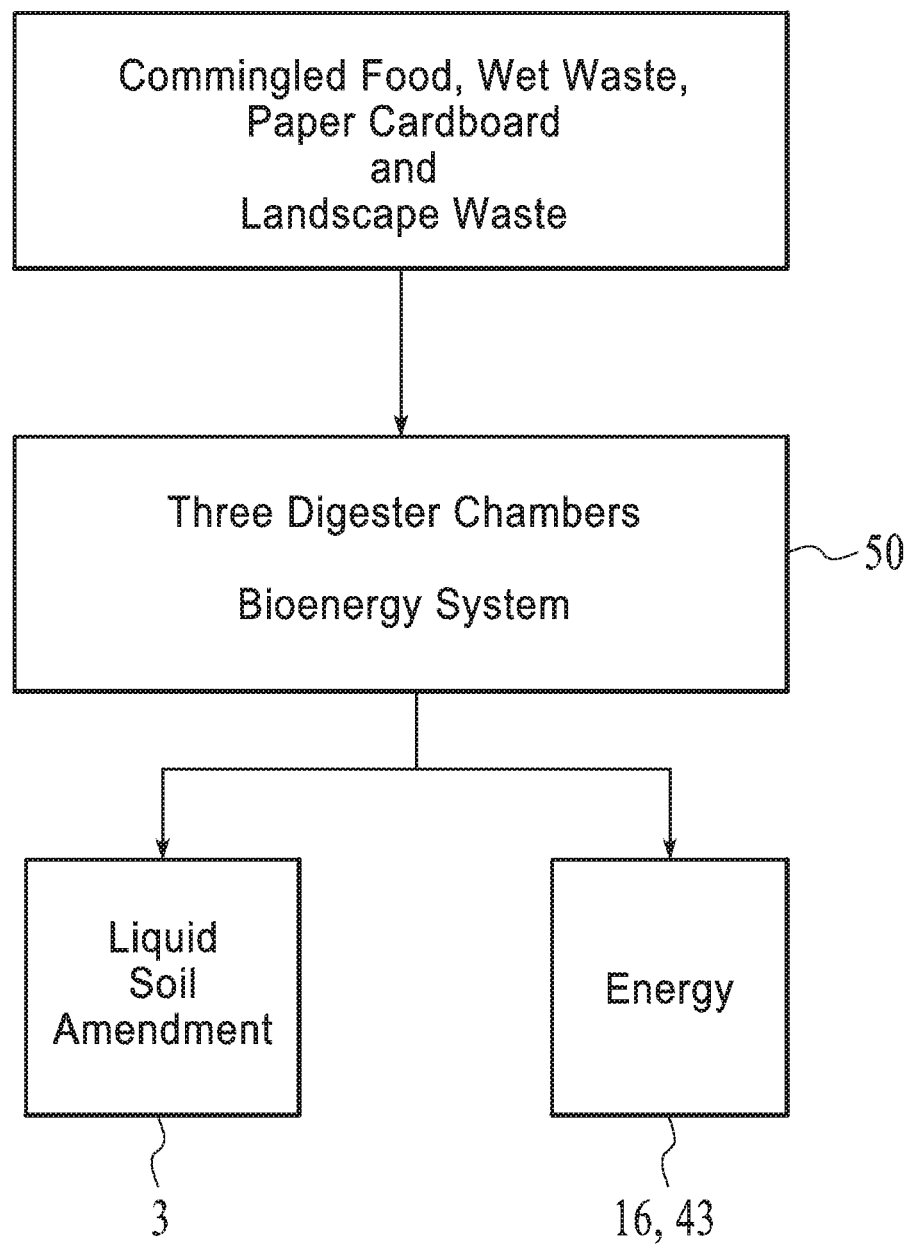

FIG. 4 shows a long cross section view through the primary module of a two-digester-chamber bio-mimicry system, with a biofilter apparatus, an organic waste processor apparatus, a blending, buffering, and dosing apparatus, an heating apparatus, a gas treatment apparatus, a surplus gas combustion apparatus, and an odor control system exhaust apparatus, according to illustrative embodiments of the present invention;

FIG. 5 shows a short cross section view through the primary module of a two-digester-chamber bio-mimicry system with a receiving, inspection, and sorting table apparatus, an organic waste processor apparatus, a digester apparatus, an odor control exhaust apparatus, and a gas storage apparatus, according to illustrative embodiments of the present invention;

FIG. 6 shows a plan view and a long cross section view through both chambers of a digester apparatus of a two-digester-chamber bio-mimicry system with a continuously stirred tank reactor zone apparatus, a fixed film packed bed reactor zone apparatus, a partition separating the two zones, a liquid level overflow control system apparatus, a biogas discharge system apparatus, and a plurality of devices for mixing, scum destruction, solids recirculation, and sampling, according to illustrative embodiments of the present invention;

FIG. 7 shows a short cross section through a second chamber and a matching elevation view of a digester apparatus showing a plurality of holes in the partition, a plurality of fittings on a downstream end of the digester, and gas discharge apparatus, according to illustrative embodiment of the present invention;

FIG. 8 shows a cross section of a pressure regulation apparatus, a safety relief apparatus, and backflow prevention apparatus within a gas treatment system, according to embodiments of the present invention;

FIG. 9 shows a long side elevation view of both sides, and a short side elevation view of a side with large access doors for a prefabricated ISO intermodal container enclosure according to embodiments of the present invention;

FIG. 10 shows a section view of a pre-grinder device that may be a first part of an organic waste processor according to embodiments of the present invention;

FIG. 11 schematically shows a solid, liquid, and gas control process diagram downstream of a pre-grinder device according to embodiments of the present invention;

FIG. 12A and FIG. 12B show a plan view and an elevation view, respectively, of a primary module of a two-digester-chamber bio-mimicry system coupled to a secondary energy storage module according to embodiments of the present invention;

FIG. 13A, FIG. 13B, and FIG. 13C show a plan view, a left side elevation view, and a left side isometric view, respectively, of a primary module of a three-digester-chamber bio mimicry system according to embodiments of the present invention;

FIG. 14 schematically shows a process flow for a three-digester-chamber bio mimicry system according to embodiments of the present invention;

FIG. 15 shows a plan view of a primary module, a secondary digester module, a tertiary gas storage module, and a quaternary double membrane spherical gas storage module, of a bio mimicry system according to embodiments of the present invention;

FIG. 16 shows a system for processing food waste and food service paper products waste inputs, representing one possible embodiment of the present invention, which utilizes a three-digester-chamber system, and outputting liquid soil amendment to a digestate liquid storage apparatus, and biogas to a biogas storage apparatus;

FIG. 17 shows a system for processing food waste, food service paper products waste, and other organic solids waste inputs, representing one possible embodiment of the present invention, which utilizes a three-digester-chamber system, and outputting liquid soil amendment to a digestate liquid storage apparatus, and biogas to a biogas storage apparatus; and FIG. 18 shows a system for processing commingled food, wet waste, paper, paper cardboard, and landscape waste inputs, representing one possible embodiment of the invention, which utilizes a three-digester-chamber system, and outputting liquid soil amendment to a digestate liquid storage apparatus, and biogas to a biogas storage apparatus.

Figure 19A:
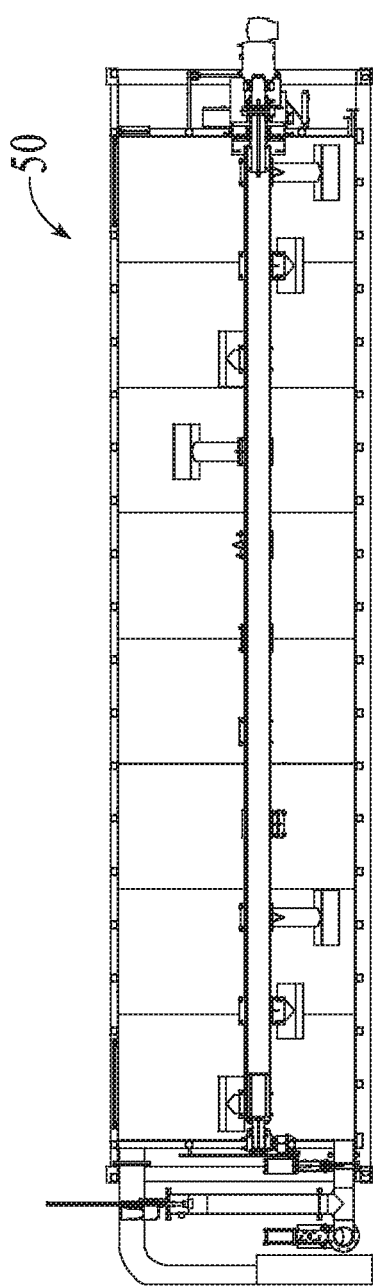
Figure 19B:
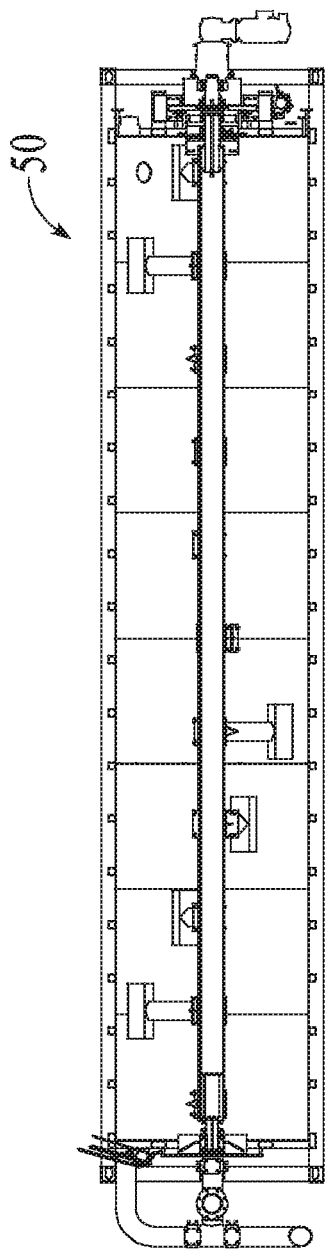
Figure 19C:
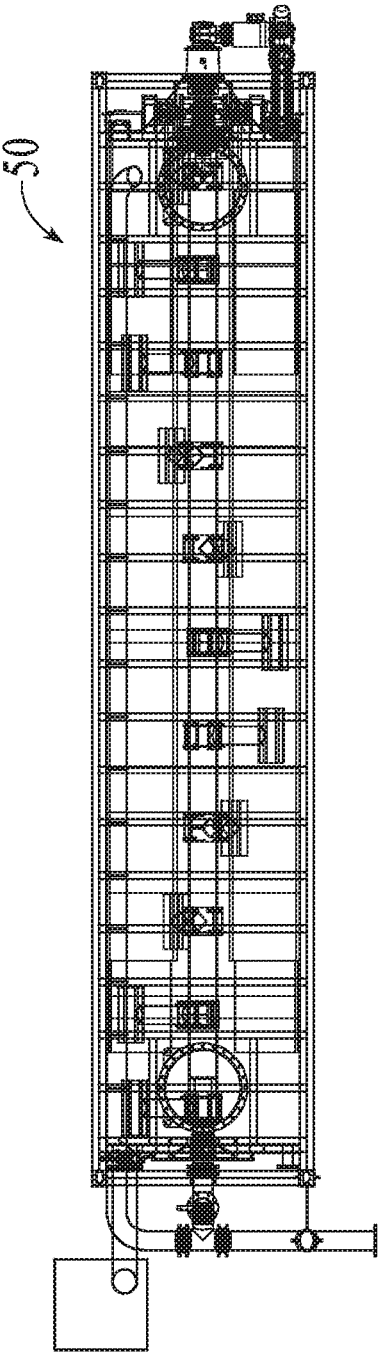
Figure 19D:
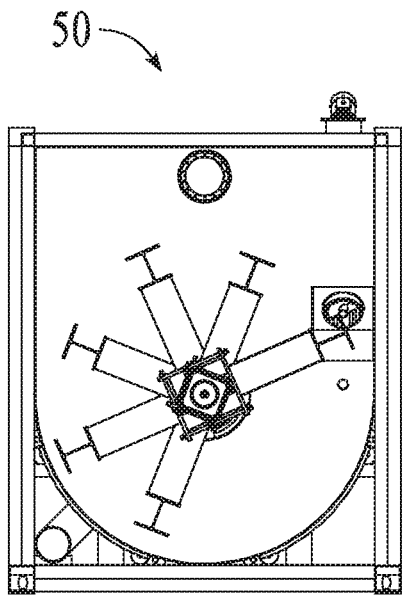
Figure 19E:
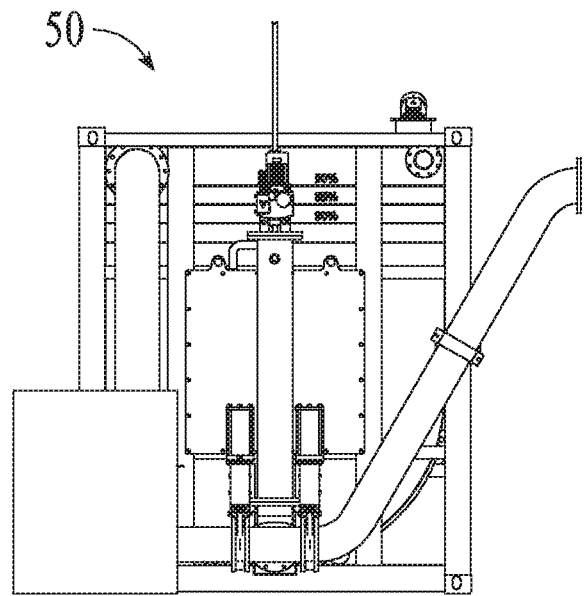
Figure 19F:
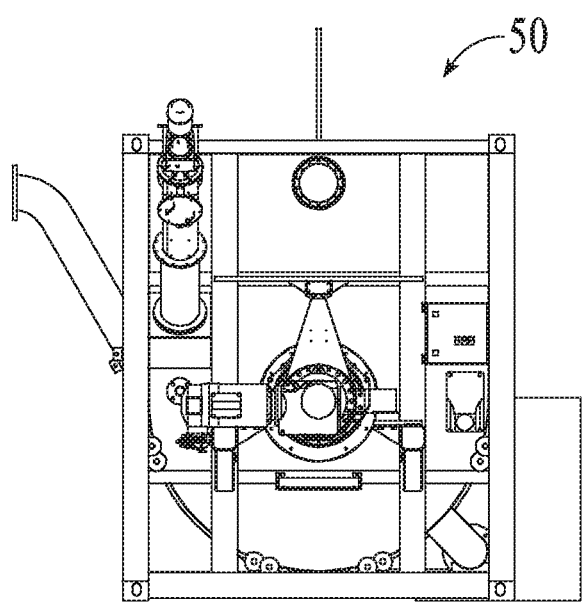

FIGS. 19A, 19B and 19C show a plan view, and FIGS. 19D, 19E and 19F show short side elevation views of both sides, of a semi-solid continuous plug flow horizontal digester.

DESCRIPTION

In the Background, Summary, and Drawings Description above, in the Description and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The terms "multi-modal" and "bio-mimicry" are used herein in a manner consistent with their respective dictionary definitions. In the context of the Background, Summary, and Drawings Description above, in the Description and the claims below, and in the accompanying drawings, a multi-modal bio-mimicry system refers to a bio-mimicry system employing more than one of the processes described.

The term "anaerobic digestion" and grammatical equivalents thereof are used herein to refer to a process of decomposition of biodegradable material that occurs using microorganisms that do not require oxygen to survive. The term "aerobic digestion" and grammatical equivalents thereof are used herein to refer to a process of decomposition of biodegradable material that occurs using microorganisms that require oxygen. The term "alternating digesting system" and grammatical equivalents thereof are used herein to refer to a process wherein anaerobic digestion is followed by aerobic digestion accomplished through forced aeration, the processes all taking place within the same vessel.

The term "trans-esterification system" and grammatical equivalents thereof are used herein to refer to a process of creating biodiesel from complex organic matter such as vegetable oil, animal oils, animal fats, tallow and waste cooking oil, wherein alcohol reacts with fatty acids to form biodiesel and crude glycerol.

The term "product package separation system" and grammatical equivalents thereof are used herein to refer to a process designed to separate organic materials from non-organic materials, including packaging materials such as plastics and paper.

The term "gasification system" and grammatical equivalents thereof are used herein to refer to a process that converts organic based carbonaceous materials into syngas (from synthesis gas), a fuel gas mixture consisting primarily of hydrogen, carbon monoxide and carbon dioxide.

The term "drying system" and grammatical equivalents thereof are used herein to refer to a process that removes moisture from sludge, sewage and digestate so the material may be used for biomass energy, organic fertilizer and compost, and animal bedding.

The term "prilling system" and grammatical equivalents thereof are used herein to refer to a process wherein the output of a digestion vessel is pelletized, transforming the material into a neater form that is simpler to handle.

The processes and modes described in the Background, Summary, and Drawings Description above, in the Description and the claims below, and in the accompanying drawings, refer to components, apparatus, steps and methods related to anaerobic digestion, aerobic digestion, alternating digestion, trans-esterification, product-package separation, gasification, drying, and prilling.

The term "comprises" and grammatical equivalents thereof are used herein to mean that other components, ingredients, steps, etc. are optionally present. For example, an article "comprising" (or "which comprises") components A, B, and C can consist of (i.e. contain only) components A, B, and C, or can contain not only components A, B, and C but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)–(a second number)," this means a range whose lower limit is the first number and whose upper limit is the second number. For example, 25 to 100 mm means a range whose lower limit is 25 mm, and whose upper limit is 100 mm.

The present invention is related to a prefabricated, multi-modal, portable, modular, bio-mimicry system, a Bioenergy System. In a Bioenergy System, one of the above-named processes, or their equivalents, rely upon another process to avoid and/or minimize hauling and disposal expense and/or environmental liability by utilizing by-product created in a first mode in subsequent modes until by-products are no longer usable or saleable. Multiple embodiments of the invention are described hereinafter with reference to the accompanying drawings. This invention may, however, be embodied in many different forms and should not be construed as limited to the embodiments set forth herein; rather, these embodiments are provided so that this disclosure will be thorough and complete and will fully convey the scope of the invention to those skilled in the art.

The embodiments of the Bioenergy System herein described include a receiving and metering tank, a first stage digester tank, blending-mixing-buffering-dosing tanks, a gravity settling and decant tank, a packed bed reactor, and a horizontal plug flow semi-solid reactor, all of which are designed as portable tanks on a common chassis or frame. The process control of the embodiments of the Bioenergy System herein described contains valves, manifolds, pumps, heating, decanting, gas conditioning system, and odor control. The entire skid mounting systems of the embodiments herein described are portable. Portable is defined as being a complete, prefabricated system, mounted on a skid or platform capable of being lifted by a crane onto a trailer or rolling stock capable of being towed by a motorized vehicle. Portable also refers to complete, prefabricated systems that can be installed within shipping containers, oil field fracturing water storage (frac) tanks or similar modules. For the embodiments of the Bioenergy System herein described, exhaust stacks extend beyond the roof for odor control, heating exhaust, and over-pressure safety relief, and a supplemental biogas burner is included for destroying excess biogas that cannot or will not be used. A gas upgrading system includes upstream desulfurization, compression, drying, heating, chilling, and filtering. The entire process control enclosure is under negative pressure and has its own two-stage odor control system, plus a high-pressure atomizing nozzle system for creating a water/neutralizing/counteracting mist. The overall system for each of the embodiments of the Bioenergy System herein described has been designed to minimize the footprint and is modular so expansion can occur with the addition of multiple systems. Raw biogas is stored on a diurnal 24-hour cycle at very low pressure which is equivalent to utility-delivered residential natural gas operating pressure of 5-10 inches water column which is 0.20-0.40 pounds per square inch.

The prefabricated apparatus of the embodiments of the Bioenergy System herein described includes the necessary mechanical equipment mounted on or installed within a skid, a platform, a trailer, a shipping container, a rail car, a frac tank or some similar structure. The embodiments of the Bioenergy System herein described also incorporate electrical equipment with a main disconnect, receiving, grinding, and pumping equipment, all piping and valves inside the skid, control package for heating and mixing, decanting valves and tank, biogas burner, mixing system, heating system, ventilation system, very low-pressure gas storage, and an electrical generator or combined heat and power unit or water boiler fueled by raw biogas.

Although a Bioenergy System can be embodied in any number of multi-modal combinations, each embodiment is a prefabricated design that can be arranged quickly in the field as shown, for example, in FIG. 1A, FIG. 1B, FIG. 2, FIG. 3, FIG. 4, FIG. 9, FIG. 12A, FIG. 12B, FIG. 13A, FIG. 13B, FIG. 13C and FIG. 15. Mechanical systems are prefabricated onto modular skids that can be transported by road, rail, sea or other means and positioned during construction. Mechanical systems include but are not limited to piping, valving, pumping, filtering, separating, and thermal conditioning for solid and semi-solids, liquid or gas circulation. Each skid is built to fit within a 25 to 350 cubic meter framework and can be lifted and installed in as little as one movement, and comes complete with connections for power, controls, inputs, and outputs minimized in number and located at the limits of the skid. In a preferred embodiment, the Bioenergy System is scaled to operate between 0.1 to 75 tons per day allowing on-site processing and eliminating the cost of hauling and transport.

The Bio-Energy system as contemplated is depicted herein in a number of embodiments. Preferred embodiments of the Bioenergy System include, but are not limited to, two-digester-chamber and three-digester-chamber systems.

Figure 1A:
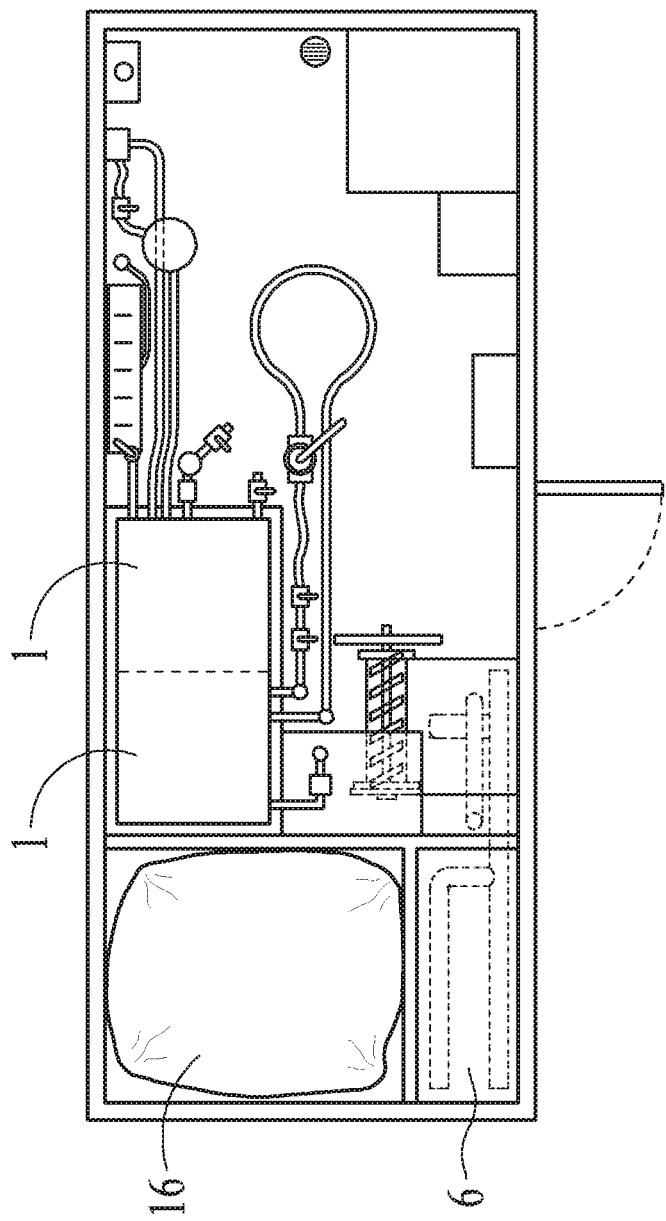
FIG. 1A shows a plan view of a primary module of a two-digester-chamber bio-mimicry system using rectangular chambers according to illustrative embodiments of the present invention.
Figure 1B:
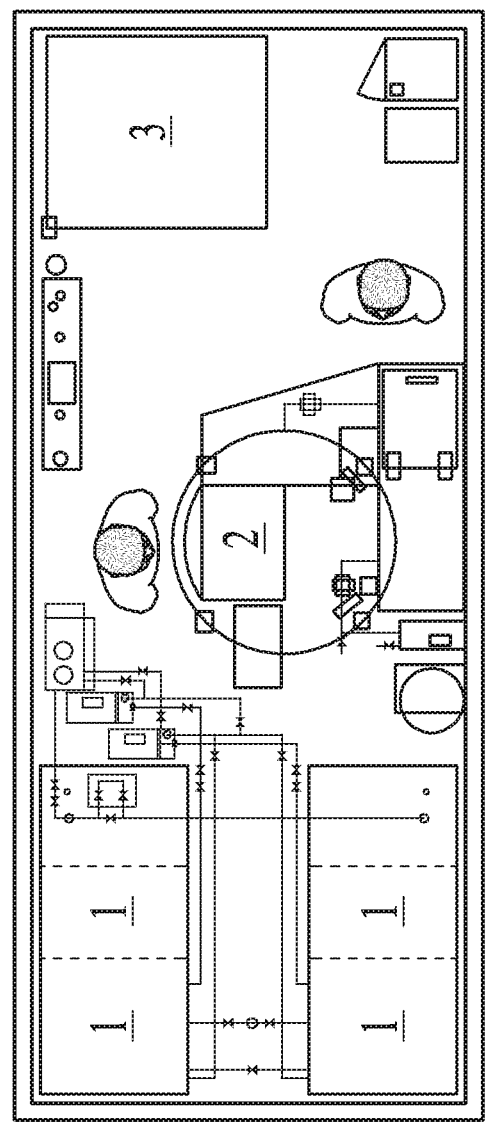
FIG. 1B shows a plan view of a primary module of a multi-modal bio-mimicry system with a large capacity waste processor and a digestate storage apparatus according to illustrative embodiments of the present invention.

Attached drawings depict a number of two-digester-chamber Bioenergy System embodiments. FIG. 1A shows one embodiment of a two-digester-chamber bio-mimicry system using rectangular chambers 1. FIG. 1B shows a plan view with a larger capacity waste processor 2 and digestate storage 3. FIG. 2 shows a plan view of a primary module of a two-digester-chamber bio-mimicry system using circular digester chambers 4 in the primary module. FIG. 3 shows a plan view of a two-digester-chamber with a larger capacity than previously illustrated 5, with a capacity expansion module, a level control apparatus 12, a mixing apparatus 13, and a digester heating apparatus 14. FIG. 4 shows a long cross section view through the primary module of a two-digester-chamber bio-mimicry system, with a biofilter apparatus for odor control 6, an organic waste processor for waste grinding, blending, buffering, and dosing 7, a heating apparatus 8, a gas treatment apparatus 9, a combustion apparatus for surplus gas 10, and an odor control system exhaust 11. FIG. 5 shows a short cross section view through the primary module of a two-digester-chamber bio-mimicry system showing receiving inspection and a sorting table allowing for the removal of contamination 15, an organic waste processor 7, a digester 1, an odor control exhaust 11, and a gas storage apparatus 16. FIG. 6 shows a plan view and a long cross section view through both chambers of a digester apparatus of a two-digester-chamber bio-mimicry system showing a continuously stirred tank reactor zone 17, a fixed film packed bed reactor zone 18, a liquid level overflow control system 19, a biogas discharge system 20, a partition 21 that regulates passage from the first to the second zone (17 to 18), and multiple couplings for mixing, scum destruction, solids recirculation, and sampling 22. FIG. 7 shows a short cross section through a second chamber and a matching elevation view of a digester apparatus showing the holes in the partition 21, and the fittings on a downstream end of a digester showing liquid discharge 23, and a gas discharge apparatus 24. FIG. 8 shows a cross section of a pressure regulation, safety relief, and backflow prevention sub-system within a gas treatment system showing a top section 25 that discharges to a surplus gas burner 10, an adjustable depth water volume 26 that both prevents backflow of atmospheric oxygen into the system and creates gas storage pressure by creating a slight backpressure in the piping from a digester 1, a gas meter 27, and a gas storage apparatus 16. FIG. 9 shows a long side elevation view of both sides, and a short side elevation view of a side with large access doors for a prefabricated ISO intermodal container enclosure showing a personnel door for normal operation 28, large doors for repair and maintenance 29, small doors for biofilter maintenance and replacement 30, natural light windows 31, and exterior panels for signage and education 32. FIG. 12 shows a plan view and an elevation view of a primary module of a two-digester-chamber bio-mimicry system coupled to a secondary energy storage module showing a digester 1, a large capacity waste processor 2, a digestate storage apparatus 3, an odor control biofilter 6, and a gas storage apparatus 16. FIG. 15 shows a plan view of a primary module 46, a secondary digester module 47, a tertiary gas storage module 48, and a quaternary double membrane spherical gas storage module 49 of a bio-mimicry system.

Another embodiment of the Bioenergy System herein described utilizes a three-stage process that can support the processing of a wet, feedstock that can be input into the system via a pump, in addition to being designed to convert food waste and food service paper products into energy. FIG. 13A, FIG. 13B, and FIG. 13C show a plan view, a left side elevation view, and a left side isometric view of a primary module of a three-digester-chamber bio mimicry system. FIG. 14 schematically shows a process flow for a three-digester-chamber bio mimicry system showing a processor 2, a dosing tank 7, a digester 1 with zones 17 and 18, a digester heating apparatus 8, a surplus gas burner 10, an odor control apparatus 6, an odor control exhaust 11, a gas storage apparatus 16, a pressure regulation apparatus 26, a gas treatment apparatus 37, 38, 39, as well as a counteractant atomizer exhaust neutralizer 42 in the exhaust stack 11. FIG. 14 also shows generators that produce renewable heat and electricity 43, a decant tank to separate solids from suspended solids in liquid using gravity 44, and a heat exchanger 45 to recover waste heat from generators 43. FIG. 16 shows a system for processing food waste and food service paper products waste, primarily noted by digester zones 17 and 18, and a digestate liquid storage apparatus 3, a biogas storage apparatus 16, and an apparatus for beneficial use 43. FIG. 17 shows a system for processing food waste, food service paper products waste, and other organic solids waste, showing digester zones 17 and 18 and 50, with 50 being a semi-solid continuous plug flow horizontal digester, depicted in FIGS. 19A to 19F, that can accommodate higher percentages of sewage sludge, manure, animal byproducts, animal mortalities, and industrial byproducts, a digestate liquid storage apparatus 3, a biogas storage apparatus 16 and an apparatus for beneficial use 43. FIG. 18 shows a system for processing commingled food, wet waste, paper, cardboard, and landscape waste; showing digester zone 50, with 50 being a semi-solid continuous plug flow horizontal digester, depicted in FIGS. 19A to 19F, that can accommodate higher percentages of cellulose (paper, cardboard, wood) and landscape waste (grass, leaves, prunings, whole plants), a digestate liquid storage apparatus 3, a biogas storage apparatus 16 and an apparatus for beneficial use 43.

One embodiment of the Bioenergy System is designed to convert food waste and food service paper products into energy and liquid soil amendment, this process being depicted in FIG. 16. In this particular embodiment, which is shown in FIG. 1A, the prefabricated anaerobic digestion system may have a receiving and metering system with an input capacity of 0.05 tons per day, which is expandable to 2.50 tons per day as also shown in FIG. 1B. These embodiments may have an output capacity of 0.4 to 15.4 cubic feet per minute of raw biogas. The embodiment discussed is designed to optimize for production of methane with maximum heating value while minimizing the system's footprint and operating cost. The equipment is capable of continuously processing a mixture of post-consumer and pre-consumer heterogeneous food wastes in either a two-stage or three-stage process. Other supplemental feedstocks may be possible to run in the system using a variety of operational techniques to increase methane yields. The system is designed with multiple stages to insure the process is reliable.

The embodiments of the Bioenergy System described accept digester feedstock input in the form of food waste with 2-inches to 12-inches minus particle size for soft material, and 1-inch to 6-inches minus particle size for bone, frozen, and hard material. The embodiment of the Bioenergy System described supports a range of 2% to 20% solids, calculated as a daily average inside the digester, with materials capable of being distributed through the system by means of a centrifugal-style pump. The embodiments of the Bioenergy System described allow for control of feedstock preparation, residence time, temperature, moisture, density, oxygen, pH, and final particle size. The embodiments described also incorporate an odor control element. FIG. 10 shows section views of a pre-grinder device that may be used with embodiments of the present invention as the first part of the organic waste processor to reduce particles to a uniformly small size, showing a vertical inlet chute 33 from the sorting table 15, a variable pitch helical screw conveyor 34 to convey and force organic waste through an orifice plate 35, and a rotating blade 36 that then discharges into the mixing, blending, buffering, and dosing tank 7. FIG. 11 schematically shows a solid, liquid, and gas control process diagram downstream of the pre-grinder device that may be used with embodiments of the present invention, showing an organic waste processor 7, a digester 1, a liquid control apparatus 19, a gas storage apparatus 16, a gas meter 27, a surplus gas burner 10, and a gas treatment apparatus consisting of a water trap 37, a gas dryer 38, a sulfur trap 39, a pressure regulation apparatus 26, a manifold control storage apparatus, an apparatus for beneficial use 40, and a flame arrestor apparatus 41 to prevent flame instruction from the surplus gas burner 10.

In the first stage of the biodegradation process, as implemented in a preferred embodiment of the Bioenergy System, the material is macerated and then pumped into a controlled anaerobic environment at a temperature between 34.0 and 37.5° C. (93-99 F) for a nominal 30-day period as calculated as volume/input rate in series through two equal sized digestion chambers inside one tank. The main digestion process takes place in a continuously stirred tank reactor; this is the largest vessel in the system. Mixing and heating is continuous in the process. Temperatures are controlled by using heat generated by the burning of biogas. In the second stage, the feedstock is pumped into an anaerobic packed bed reactor and then either before or after, at the operator's discretion, into a gravity settling and decant tank for additional conversion. In the third stage, the feedstock is conveyed into a semi-solid phase continuous plug flow horizontal digester that can accommodate higher percentages of fibrous or otherwise un-pumpable material. The operator has the ability and discretion to measure inputs and outputs, inspect feedstock for contamination, operate the macerator, adjust pumping rates and schedules, adjust temperature, take samples, and measure digester process chemistry, etc. Full wireless communication and automation of pumping, heating, and chemistry is part of the control design.

A person having ordinary skill in the art will understand that, in any of the embodiments described above and any obvious variation thereof, any non-saleable or by-products can be re-used in an appropriate system until saleable material has been obtained and/or by-product can no longer be used in a subsequent mode.

The invention claimed is:

1. A prefabricated, multi-modal, portable, modular, bio-mimicry system, with an external framework not exceeding 350 cubic meters, the system comprising:
   a. a process control system is comprised of valves, manifolds, pumps, heating, decanting, gas conditioning system, and odor control and a process control enclosure;
   b. a plurality of bio-mimicry vessels chosen from a group comprised of an anaerobic digester, an aerobic digester, an alternating digester, a trans-esterification system, a product package separation system, a gasification system, a drying system, and a prilling system;
   c. a gas control system, comprising a gas volume meter, a manifold, a gas dryer, a pressure regulator, a flame arrester, a Sulphur trap, a Sulphur burner, and a water trap;
   d. a liquid control system is comprised of a liquid manifold and a volume meter;
   e. a liquid storage vessel;
   f. an energy generation system; and
   g. an energy storage vessel.

2. The prefabricated, portable, modular, multi-modal bio-mimicry system of claim 1, where the anaerobic digester, aerobic digester, or alternating digester accepts a feedstock where the feedstock falls within a range of 1 cubic millimeter and 200 cubic millimeters; where the anaerobic digester, aerobic digester, alternating digester accepts a dosing volume; where the dosing volume is adjustable within a range of 0.21% of volume and 1.67% of volume; and where the frequency of digester dosing is adjustable within a range of 1.2 hours to 9.6 hours; and where the bulk density of feedstock accepted may range from 400 kg/cubic meter to 1,200 kg/cubic meter, and where the moisture content of feedstock accepted may range from 0.5% of solids to 40.0% of solids.

3. The prefabricated, portable, modular, multi-modal bio-mimicry system of claim 2 where a first bio-mimicry vessel is preceded by a plurality of unit processes; where the unit processes include either a sorting table, or a grinding apparatus, or a mixing apparatus, or a blending tank, or a buffering apparatus, or a dosing chamber, or a first stage continuously stirred tank reactor chamber, or a second stage packed bed tank reactor chamber, or an alternative bypass chamber leading to a continuously fed horizontal plug flow reactor for fibrous and un-pumpable organic waste, or any combination thereof.

4. The prefabricated, portable, modular, multi-modal bio-mimicry system of claim 3, wherein a dosing chamber, a first stage continuously stirred tank reactor chamber, a second stage packed bed tank reactor, and an alternative bypass chamber are included, and the dosing chamber has a hydraulic residence time of at least 12%, the first stage continuously stirred tank reactor chamber has a hydraulic residence time of at least 66%, the second stage packed bed tank reactor chamber has a hydraulic residence time of at least 22%, and the alternative bypass chamber has a hydraulic residence time of at least 88%.

5. The prefabricated, portable, modular, multi-modal bio-mimicry system of claim 4, wherein the first stage continuously stirred tank reactor chamber, the second stage packed bed tank reactor chamber, and the alternative bypass chamber are heated to mesophilic or thermophilic temperatures.

6. The prefabricated, portable, modular, multi-modal bio-mimicry system of claim 5, wherein the bio-mimicry vessels include at least one of an anaerobic digester, an aerobic digester, or an alternating system.

7. The prefabricated, portable, modular, multi-modal bio-mimicry system of claim 5, wherein the bio-mimicry vessels include at least an anaerobic digester and at least a drying system.

8. The prefabricated, portable, modular, multi-modal bio-mimicry system of claim 7, wherein at least one bio-mimicry vessel is a product package separation system.

9. The prefabricated, portable, modular, multi-modal bio-mimicry system of claim 8, wherein the bio-mimicry vessels include at least one prilling system.

10. The prefabricated, portable, modular, multi-modal bio-mimicry system of claim 7, wherein the bio-mimicry vessels include at least one trans-esterification system, the trans-esterification system being further comprised of a transfer and metering container and a glycerin storage receptacle, and where the trans-esterification system processes: uncontaminated pure food without any contamination or packaging; food commingled with plastic; compostable plastic, glass, ceramic, metal, or other materials; packaged food still in its container, bag, can, box, bottle, or other package.

11. The prefabricated, portable, modular, multi-modal bio-mimicry system of claim 10, wherein the bio-mimicry vessels include at least one prilling system.

12. The prefabricated, portable, modular, multi-modal bio-mimicry system of claim 7, wherein the bio-mimicry vessels include at least one gasification system and at least one prilling system.

13. The prefabricated, portable, modular, multi-modal bio-mimicry system of claim 5, wherein the bio-mimicry vessels include at least an anaerobic digester and an aerobic digester.

14. The prefabricated, portable, modular, multi-modal bio-mimicry system of claim 13, wherein at least one bio-mimicry vessel is a product package separation system.

15. The prefabricated, portable, modular, multi-modal bio-mimicry system of claim 5, wherein the bio-mimicry vessels include at least one anaerobic digester and at least one alternating system.

16. The prefabricated, portable, modular, multi-modal bio-mimicry system of claim 15, wherein the bio-mimicry vessels include at least one aerobic digester.

17. The prefabricated, portable, modular, multi-modal bio-mimicry system of claim 16, wherein the bio-mimicry vessels include at least one gasification system.

18. A method for biodegrading food waste, food service paper products, wet waste, paper cardboard, landscape waste, and other organic solids employing by-product synergy, comprising the acts of:
  a. Inputting feedstock comprising food waste, food service paper products, wet waste, paper cardboard, landscape waste, or other organic solids into a prefabricated, portable, modular, multi-modal bio-mimicry apparatus of claim 1;
  b. Processing the feedstock utilizing a first bio-mimicry vessel of the prefabricated, portable, modular, multi-modal bio-mimicry apparatus, where output includes organic materials, fats, oil, grease, packaging in consumer product form, or small plastic particles;
  c. Processing the output of the first bio-mimicry vessel of the prefabricated, portable, modular, multi-modal bio-mimicry apparatus, where output includes organic materials, fats, oil, grease, packaging in consumer product form, and small plastic particles, utilizing a second bio-mimicry vessel directly connected to the first bio-mimicry vessel, where output includes organic materials, fats, oil, grease, bio-diesel or syngas;
  d. Storing the organic materials, fats, oil, grease, bio-diesel, or syngas output by the second bio-mimicry vessel of the prefabricated, portable, modular, multi-modal bio-mimicry apparatus.

19. A method for biodegrading food waste, food service paper products, wet waste, paper cardboard, landscape waste, and other organic solids employing by-product synergy, comprising the acts of:
  a. Inputting feedstock comprising food waste, food service paper products, wet waste, paper cardboard, landscape waste, or other organic solids into a prefabricated, portable, modular, multi-modal bio-mimicry apparatus of claim 1;
  b. Processing the feedstock f utilizing a first bio-mimicry vessel of the prefabricated, portable, modular, multi-modal bio-mimicry apparatus, where output includes organic materials, fats, oil, grease, packaging in consumer product form, or small plastic particles;
  c. Processing the output of the first bio-mimicry vessel of the prefabricated, portable, modular, multi-modal bio-mimicry apparatus, where output includes organic materials, fats, oil, grease, packaging in consumer product form, and small plastic particles, utilizing a second bio-mimicry vessel directly connected to the first bio-mimicry vessel, where output includes organic materials, fats, oil, grease, bio-diesel or syngas;
  d. Processing the output of the second bio-mimicry vessel of the prefabricated, portable, modular, multi-modal bio-mimicry apparatus, where output includes organic materials, fats, oil, grease, bio-diesel or syngas, utilizing a third bio-mimicry vessel directly connected to the second bio-mimicry vessel, where output includes organic materials, fats, oil, grease, bio-diesel or syngas;
  e. Storing the organic materials, fats, oil, grease, bio-diesel or syngas output by the third bio-mimicry vessel of the prefabricated, portable, modular, multi-modal bio-mimicry apparatus.

20. A method for biodegrading food waste, food service paper products, wet waste, paper cardboard, landscape waste, and other organic solids employing by-product synergy, comprising the acts of:
  a. Inputting feedstock comprising food waste, food service paper products, wet waste, paper cardboard, landscape waste, or other organic solids into a prefabricated, portable, modular, multi-modal bio-mimicry apparatus of claim 1;
  b. Processing the feedstock utilizing a first bio-mimicry vessel of the prefabricated, portable, modular, multi-modal bio-mimicry apparatus, where output includes organic materials, fats, oil, grease, packaging in consumer product form, or small plastic particles;
  c. Processing the output of the first bio-mimicry vessel of the prefabricated, portable, modular, multi-odal bio-mimicry apparatus, where output includes organic materials, fats, oil, grease, packaging in consumer product form, and small plastic particles, utilizing a second bio-mimicry vessel directly connected to the first bio-mimicry vessel, where output includes organic materials, fats, oil, grease, bio-diesel or syngas;
  d. Processing the output of the second bio-mimicry vessel of the prefabricated, portable, modular, multi-modal bio-mimicry apparatus, where output includes organic materials, fats, oil, grease, bio-diesel or syngas, utilizing a third bio-mimicry vessel directly connected to the second bio-mimicry vessel, where output includes organic materials, fats, oil, grease, biogas or bio-diesel;

e. Processing the output of the third bio-mimicry vessel of the prefabricated, portable, modular, multi-modal bio-mimicry apparatus, where output includes organic materials, fats, oil, grease, bio-diesel or syngas, utilizing a fourth bio-mimicry vessel directly connected to the third bio-mimicry vessel, where output includes organic materials, fats, oil, grease, bio-diesel or syngas;
f. Storing the organic materials, fats, oil, grease, biogas, or bio-diesel output by the third bio-mimicry vessel of the prefabricated, portable, modular, multi-modal bio-mimicry apparatus.

\* \* \* \* \*